United States Patent [19]

Chabala et al.

[11] Patent Number: 4,806,564
[45] Date of Patent: Feb. 21, 1989

[54] ANTIHYPERCHOLESTEROLEMIC BETA-LACTONES

[75] Inventors: John C. Chabala, Westfield; Yuan-Ching P. Chiang, Piscataway; Michael N. Chang, Westfield; Donald W. Graham, Mountainside, James V. Heck, Scotch Plains, Shu S. Yang, Bridewater, all of N.J.

[73] Assignee: Merck & Co., Inc., Rahway, N.J.

[21] Appl. No.: 53,774

[22] Filed: May 26, 1987

[51] Int. Cl.$^4$ .................. A61K 31/365; C07D 305/08
[52] U.S. Cl. ..................... 514/449; 549/263; 549/328
[58] Field of Search ................ 549/263, 327, 328; 514/449

[56] References Cited

U.S. PATENT DOCUMENTS

| 4,358,602 | 11/1982 | Umezawa et al. | 549/328 |
| 4,598,089 | 7/1986 | Haduary et al. | 549/263 |
| 4,751,237 | 6/1988 | Chabala et al. | 514/449 |

FOREIGN PATENT DOCUMENTS 0185359  6/1986  European Pat. Off. ............ 549/328

OTHER PUBLICATIONS

Chemical Communications, 1970, p. 639 [(Chem. Abstracts; vol. 73 #55594j (1970)].
J. Chem. Soc. (c), 1971, pp. 3888–3890 [(Chem. Abstracts; vol. 76, #45686)].

*Primary Examiner*—Glennon H. Hollrah
*Assistant Examiner*—S. Treanor
*Attorney, Agent, or Firm*—Joseph F. DiPrima; Michael C. Sudol

[57] ABSTRACT

The compounds of the following structural formula (I)

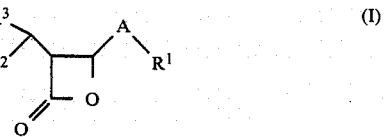

are 3-hydroxy-3-methylglutaryl-coenzyme A (HMG-CoA) synthase inhibitors and useful as antihypercholesterolemic agents for the treatmet of disease in which the inhibition of cholesterol biosynthesis would be useful, such as arteriosclerosis, hyperlipidemia and familial hypercholesterolemia.

22 Claims, No Drawings

ANTIHYPERCHOLESTEROLEMIC BETA-LACTONES

BACKGROUND OF THE INVENTION

The compound of the formula (I), wherein $R^1$ is carboxy, $R^2$ are hydroxy, and A is 2,4,6-trimethyl-deca-2,4-dien-1,10-diyl, 12-hydroxy-13-hydroxymethyl-3,5,7-trimethyltetradeca-2,4-dien-1,14-dioic acid 12,14-lactone, was identified as an antibiotic fungal metabolite in 1970 [Aldridge et al., *Chem. Comm.*, 1970, p. 639]. The methyl ester of this compound and its tetrahydro analog were disclosed in the structure elucidation of this compound [Aldridge et al. *J. Chem. Soc.* (C), 1971, pp. 3888–3891].

Additionally, co-pending patent application Ser. No. 856,316, filed Apr. 28, 1986 is directed to the antihypercholesterolemic utility of these known compounds and co-pending patent application Ser. No.021,848, filed Mar. 4, 1987, discloses novel β-lactone derivatives and their anti-hypercholesterolemic utility.

SUMMARY OF THE INVENTION

This invention relates to the novel compounds of the formula (I) and the pharmacological properties of these compounds which have been found to be HMG-CoA synthase inhibitors and useful as antihypercholesterolemic agents either as the sole therapeutic agent or in combination with bile acid sequestrants.

DETAILED DESCRIPTION OF THE INVENTION

The present invention is directed to novel compounds represented by the following general structural formula (I):

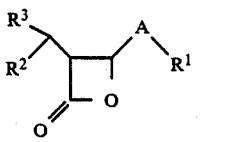

wherein:
$R^1$ is selected from
 (1) hydrogen,
 (2) hydroxy,
 (3) $C_{1-6}$ alkoxy,
 (4) phenyl,
 (5) carboxy,
 (6) $C_{1-6}$ alkoxycarbonyl,
 (7) substituted $C_{1-6}$ alkoxycarbonyl in which the substituent is a phenyl group,
 (8) aminocarbonyl,
 (9) $C_{1-6}$ alkylaminocarbonyl,
 (10) substituted $C_{1-6}$ alkylaminocarbonyl in which the substituent is a hydroxy group,
 (11) phenylaminocarbonyl,
$R^2$ is selected from
 (1) hydrogen,
 (2) $C_{1-6}$ alkyl,
 (3) $C_{1-6}$ alkyloxy,
 (4) $C_{2-6}$ alkenyloxy,
 (5) formyloxy,
 (6) $C_{1-6}$ alkylcarbonyloxy,
 (7) carboxy $C_{1-6}$ alkylcarbonyloxy,
 (8) anisyldiphenylmethyloxy,
 (9) $C_{1-6}$ alkylsulfonyloxy,
 (10) aminocarbonyloxy, and
 (11) $C_{1-6}$ alkylaminocarbonyloxy;
$R^3$ is selected from
 (1) hydrogen,
 (2) $C_{1-6}$ alkyl,
 (3) $C_{1-6}$ alkenyl,
 (4) phenyl, or
$R^2$ and $R^3$ when taken together with the carbon atom to which the are attached form $C_{3-6}$ carbocyclic ring;
A is selected from
 (1) $C_{1-17}$ alkylene, straight chain or branched chain,
 (2) substituted $C_{1-17}$ alkylene in which the one or two substituents are
  (a) oxo,
  (b) epoxy,
  (c) geminal dihydroxy,
  (d) $C_{1-6}$ alkoxy, and
  (e) 4-bromophenylhydrazono;
 (3) monounsaturated $C_{6-17}$ alkylene, and
 (4) substituted mnnounsaturated $C_{6-17}$ alkylene in which the one or two substituents are
  (a) oxo,
  (b) epoxy,
  (c) geminal dihydroxy,
  (d) $C_{1-6}$ alkoxy, and
  (e) 4-bromophenylhydrazono;
 (5) $C_{7-16}$ aralkylene, wherein the alkyl chain is interupted by a 1,2-, 1,3-, or 1,4-phenylene moiety,
 (6) $C_{6-18}$ alkylene, straight or branched chain, interupted by an oxygen, sulfur or sulfoxide moiety,
 (7) a group of the structure

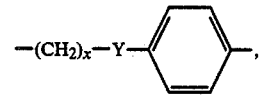

where x is 1–4 and Y is O, S, or SO; and pharmaceutically acceptable salts thereof.

One embodiment of the compounds of the present invention is the class of compounds of the formula (I) wherein A is $C_{6-17}$ alkylene. Exemplifying this embodiment are the following compounds:
 (1) E-3-methyl-4-(5-phenylpentyl)-2-oxetanone
 (2) E-3-methyl-4-(6-phenylhexyl)-2-oxetanone
 (3) E-3-methyl-4-(9-phenylnonyl)-2-oxetanone
 (4) E-3-methyl-decyl-2-oxetanone A second embodiment of the compounds of the present invention is the class of compounds of the formula (I) wherein A is substituted $C_{6-17}$ alkylene. Exemplifying this embodiment are the following compounds:
 (1) 8-(3-hydroxymethyl-4-oxo-2-oxetanyl)-4-methyl-2-octanone
 (2) 8-(3-hydroxymethyl-4-oxo-2-oxetanyl)-4-methyl-2-(4-bromophenylhydrazono)-octane
 (3) 8-(3-methoxymethyl-4-oxo-2-oxetanyl)-4-methyl-2-octanone
 (4) 8-(3-methoxymethyl-4-oxo-2-oxetanyl)-4-methyl-2-methoxyoctane
 (5) 8-(3-methoxymethyl-4-oxo-2-oxetanyl)-4-methyl-2-octanol
 (6) E-3-methyl-4-(9-oxodecyl)-2-oxetanone.

A third embodiment of the compounds of the present invention is the class of compounds of the formula (I) wherein A is monounsaturated $C_{6-17}$ alkylene. Exemplifying this embodiment is the following compound:

(1) E-3-methyl-4-(9-decenyl)-2-oxetanone.

A fourth embodiment of the compounds of the present invention is the class compounds of the formula (I) wherein A is substituted monounsaturated $C_{6-17}$ alkylene. Exemplifying this embodiment are the following compounds:

(1) methyl 11-(3-hydroxymethyl-4-oxo-2-oxetanyl)-4,5-oxiranyl-3,5,7-trimethyl-2-undecenoate
(2) 11-(3-hydroxymethyl-4-oxo-2-oxetanyl)-4,5-oxiranyl-3,5,7-trimethyl-2-undecenoic acid
(3) methyl 11-(3-hydroxymethyl-4-oxo-2-oxetanyl)-4,5-dihdroxy-3,5,7-trimethyl-2-undecenoate
(4) methyl 11-(3-methoxymethyl-4-oxo-2-oxetanyl)-4,5-dihdroxy-3,5,7-trimethyl-2-undecenoate The present invention is also directed to a method of inhibiting cholesterol biosynthesis which comprises the administration to a subject in need of such treatment a nontoxic therapeutically effective amount of a compound represented by the following general structural formula (I) and pharmaceutically acceptable salts thereof.

The present invention is also directed to a method of inhibiting the activity of HMG-CoA synthase enzyme which comprises the administration to a subject in need of such treatment a nontoxic therapeutically effective amount of a compound represented by the general structural formula (I) and pharmaceutically acceptable salts thereof.

Specifically the compounds of this invention are useful as antihypercholesterolemic agents for the treatment of arteriosclerosis, hyperlipidemia, familiar hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

Wherein $R^1$ is hydrogen or phenyl and A is not substituted with an oxo, an epoxy or a 4-bromophenylhydrazono, the compounds of the formula (I) wherein $R^2$ is hydrogen, that is the 3-methyl-4-substituted-2-oxetanones, are conveniently prepared from readily available starting materials as described in the following synthetic pathway:

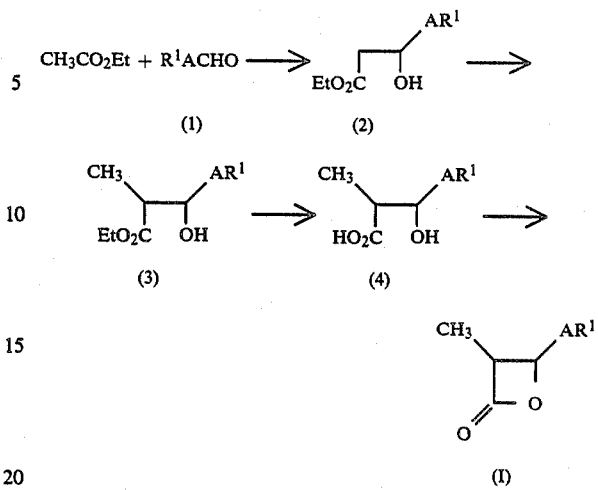

wherein $R^2$ is hydrogen.

Ethyl acetate is reacted with an appropriately substituted aldehyde (1) wherein $R^1$ is hydrogen or phenyl and A is not substituted with an oxo, epoxy or 4-bromophenylhydrazono in the presence of two moles of lithium diisopropylamide to the β-hydroxy ester (2) in its dianion form. The dianion is alkylated with methyl iodide to give the β-hydroxy ester. Base hydrolysis of the β-hydroxy ester (3) to yield (4) is followed by a standard lactonization to give the compounds of the formula (I) wherein $R^2$ is hydrogen. When A is substituted with an oxo, an epoxy or a 4-bromophenylhydrazono, a mono or diunsaturated is further elaborated by a selective bromination dehydrobromination followed by oxidation to the oxo substituted compounds which are transformed to the epoxy substituted and 4-bromophenylhydrazono substituted compounds under standard reaction conditions.

The compounds of the formula (I) wherein $R^2$ is hydroxy or $C_{1-6}$ alkoxy are conveniently prepared from the known compound, 12-hydroxy-13-hydroxymethyl-3,5,7-trimethyltetradeca-2,4-dien-1,14 dioic acid 12,14-lactone (II) or its alkyl ester according to the following synthetic transformations.

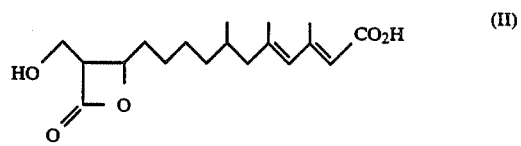

When A is substituted with an epoxy group, the compound of the formula (II) or its $C_{1-6}$ alkyl ester is reacted with m-chloroperbenzoic acid. When A is substituted with a geminal dihydroxy group, the compound of the formula (II) or its $C_{1-6}$ alkyl ester is reacted with osmium tetroxide. When A is substituted with an oxo group the 13-$C_{1-6}$ alkoxymethyl derivative of the compound of the formula (II) is reacted with ozone. The 13-$C_{1-6}$ alkoxymethyl derivatives may be prepared by the alkylation of the hydroxymethyl group with an alkyl halide in the presence of silver oxide. The oxo substituted compounds can be converted into the $C_{1-6}$ alkoxy substituted compounds by reduction to the hydroxy followed by an alkylation under standard conditions. The oxo compound can also be converted into the 4-bromophenylhydrazono compound using standard reaction conditions.

The intrinsic HMG-CoA synthase inhibition activity of the compounds of this invention is measured by the standard in vitro protocol described below:

The livers from male Charles River CD rats (225–350 g) were homogenized in 0.25 M sucrose which was adjusted with phenylmethylsulfonylfluoride (PMSF) and N-p-tosyl-1-lysine chloromethyl ketone (TLCK) so that the final concentration of each was 50 and 25 mg/ml, respectively. The homogenate was centrifuged at 15,000× g for 20 minutes, the supernatant filtered through a fine nylon screen to remove most of the fat layer and recentrifuged at 100,000× g for 1 hour. This supernatant was removed and 1 M potassium phosphate, dithiothreitol (DTT) and ethylene glycol-bis($\beta$-aminoethyl ether)-N,N,N',N'-tetracetic acid (EGTA) added to give a final concentration of 0.1 M (pH 7.2), 0.5 mM and 0.1 mM, respectively. Solid ammonium sulfate was added to 50% saturation to the protein solution, it was centrifuged at 15,000× g and the supernatant discarded. This precipitated protein could be stored at $-70°$ C. for at least one month with very little loss of activity. The ammonium sulfate precipitate was dissolved in an minimal mount of 0.06 M potassium phosphate buffer (pH 7.2) containing 0.5 mM dithiothreitol and 0.1 mM EGTA (referred to as 0.06 M phosphate buffer) and dialyzed overnight against 2 liters of the same buffer to remove the ammonium sulfate and to inactivate HMG-CoA lyase [Clinkenbeard, et al., J. Biol. Chem. 250, 3108–3116(1975)].

The dialyzed extract was added to a column of DEAE-52 (Whatman) which had been equilibrated with 0.06 M phosphate buffer (10 mg of protein to 1 ml bed volume of the resin). The DEAE-cellulose was eluted with 0.06 M phosphate buffer until the optical density at 280 nm was essentially zero. This fraction contained the $\beta$-ketoacetyl-CoA thiolase activity. The HMG-CoA synthase was eluted from the column with 0.1 M phosphate buffer (pH 7.2) containing 0.5 mM DTT and 0.1 mM EGTA, and was virtually free of all thiolase activity. The protein was precipitated by the addition of ammonium sulfate to give 50% saturation. This solution was stirred for 10 minutes at 4° C. and the precipitate collected by centrifugation at 15,000 rpm for 10 minutes. The supernatant was discarded and the precipitate dissolved in a minimum of 0.06 M phosphate buffer, pH 7.2 (about 10 ml) and the enzyme stored at $-80°$ C.

HMG-CoA Synthase Inhibition Assay

Enzyme protein (ca. 24 mg) was added to a solution containing 117 $\mu$M Tris-HCl (pH 8.0), 11.7 $\mu$M MgCl$_2$, 1.17 $\mu$M Ethylenediaminetetraacetic acid (EDTA), 0.58 $\mu$M dithiothreitol, and the indicated concentrations of the test compound (added as a 2 mg/ml solution in dimethylsulfoxide). The incubation took place in a volume of 0.085 ml at 30° in a shaking water bath. After 5 minutes, 15 ml of a solution containing acetoacetyl-CoA and 0.1 $\mu$Ci of 1-[$^{14}$C]-acetyl-CoA was added to give a final concentrations of 0.1 and 0.4 $\mu$M, respectively. The incubation was continued for 10 more minutes and the reaction stopped by the addition of 50 ml of the assay mixture to 0.2 ml of 6N HCl in a glass scintillation vial. The vial was heated for 1 hour at 120° after which time 0.2 ml more of 6N HCl was again added to each vial and the heating continued for another hour. Following this, 1.0 ml of 0.9% saline was added to each vial and finally 10 ml of scintillation liquid. Radioactivity was determined in a Packard Tri-Carb liquid scintillation counter.

Percent inhibition is calculated by the formula:

$$1 - \frac{\text{Sample} - \text{Blank}}{\text{Control} - \text{Blank}}$$

IC$_{50}$ values were determined by plotting the log of the concentration of the test compound verses the percentage inhibition and fitting a straight line to the resulting data by using the least squares method.

Representative of the intrinsic HMG-CoA synthase inhibitory activities of the compounds of this invention, tabulated below are the IC$_{50}$ or IC$_{25}$ (the inhibitory concentration which inhibits 50 percent and 25 percent of the HMG-CoA synthase activity respectively).

| Compounds of the Formula (I) | | |
|---|---|---|
| AR$^1$ | R$_2$ | IC$_{50}$ |
| (CH$_2$)$_5$Ph | H | $1.4 \times 10^{-6}$ |
| (CH$_2$)$_6$Ph | H | $1.5 \times 10^{-6}$ |
| (CH$_2$)$_9$Ph | H | $1.2 \times 10^{-6}$ |
| (CH$_2$)$_9$CH$_3$ | H | $2.5 \times 10^{-7}$ |
| (CH$_2$)$_4$CH(CH$_3$)CH$_2$C(O)CH$_3$ | OH | $1.6 \times 10^{-6}$ |
| (CH$_2$)$_4$CH(CH$_3$)CH$_2$C(CH$_3$)=N-NH-C$_6$H$_4$-Br | OH | $0.8 \times 10^{-6}$ |
| (CH$_2$)$_4$CH(CH$_3$)CH$_2$C(O)CH$_3$ | OCH$_3$ | $1.7 \times 10^{-6}$ |
| (CH$_2$)$_4$CH(CH$_3$)CH$_2$CH(OCH$_3$)CH$_3$ | OCH$_3$ | $5.5 \times 10^{-6}$ |
| (CH$_2$)$_8$CH=CH$_2$ | H | $1.6 \times 10^{-6}$ |
| (CH$_2$)$_4$CH(CH$_3$)CH$_2$C(CH$_3$)(—O—)CH(CH$_3$)CH=CHCO$_2$CH$_3$ (epoxide) | OH | $0.8 \times 10^{-7}$ |
| (CH$_2$)$_4$CH(CH$_3$)CH$_2$C(CH$_3$)(—O—)CH(CH$_3$)CH=CHCO$_2$H (epoxide) | OH | $0.1 \times 10^{-6}$ |
| (CH$_2$)$_4$CH(CH$_3$)CH$_2$C(CH$_3$)(OH)—CH(CH$_3$)(OH)—CH=CHCO$_2$CH$_3$ | OH | $1.1 \times 10^{-6}$ |
| (CH$_2$)$_4$CH(CH$_3$)CH$_2$C(CH$_3$)(OH)—CH(CH$_3$)(OH)—CH=CHCO$_2$CH$_3$ | OCH$_3$ | $1.9 \times 10^{-6}$ |

The following examples illustrate the preparation of the compounds and their incorporation into pharmaceutical compositions and as such are not to be construed as limiting the invention set forth in the claims appended hereto.

EXAMPLES 1 to 6

Preparation of E-3-methyl-4-(substituted)-2-oxetanones

1. Ethyl threo-3-hydroxy-2-methyl-12-tridecenoate

To 8.6 ml g 1.0M lithium diisopropylamide (LDA), prepared from 2.20 ml of diisopropylamine, 6.3 ml of 2.5N nBuLi in hexane, and 9.5 ml of THF was added ethyl acetate (0.7325 ml, 7.5 mmoles) dropwise maintaining the temperature $< -45°$ C. After 10 minutes, 10-undecenal (1.09 g, 6.5 mmoles) was added dropwise keeping the temperature $< -30°$ C. The temperature was allowed to rise to $-15°$ C., kept there for 15 minutes, lowered to $-50°$ C. and 9.4 ml of the above LDA solution was added maintaining the temperature $< -30°$ C. After 15 minutes at $-20°$ C., the cooling bath was removed and a solution of MeI (0.70 ml, 11.25 mmoles) in HMPA (1.75 ml) was added rapidly. After 15 minutes at room temperature, the mixture was warmed at 35° C. for 5 minutes and poured into 1M $H_2SO_4$ (45 ml) and $Et_2O$ (25 ml). The aqueous phase was extracted with $Et_2O$ (2×), and the combined $Et_2O$ phases were washed with $H_2O$ (2×) and saturated brine and dried ($MgSO_4$). The crude material after evaporation in vacuo was flashed chromatographed on silica gel with hexane - EtOAc (9:1) to give pure ethyl threo-3-hydroxy-2-methyl-12-tridecenoate.

NMR: ($CDCl_3$)δ 5.80 (m, 1H, CH=$CH_2$), 4.94–5.03 (m, 2H, CH=$CH_2$), 4.16 (q, 2H, $OCH_2CH_3$), 3.64 (m, 1H, CHOH), 2.57 (d, 1H, OH), 2.50 (m, 1H, CHCH$_3$), 2.02 (q, 2H, $CH_2$CH=), 1.27 (t, 3H, $OCH_2CH_3$), 1.19 (d, 3H, $CH_3$CH).

The following compounds were prepared using essentially the same method:

Ethyl threo-3-hydroxy-2-methyltridecanoate

NMR: δ 4.17 (q, 2H, $OCH_2CH_3$), 3.64 (brs, 1H, CHOH), 2.57 (d, 1H, OH), 2.50 (m, 1H, CHCH$_3$), 1.26 (t, 2H, $OCH_2CH_3$), 1.21 (d, 3H, CHCH$_3$), 0.88 (t, 3H, 13-CH$_3$).

Ethyl threo-3-hydroxy-2-methyl-7-phenyloctanoate

NMR: δ 7.1–7.4 (m, 5H, ArH), 4.17 (q, 2H, $OCH_2CH_3$), 3.64 (brs, 1H, CHOH), 2.61 (t, 2H, $CH_2$Ph), 2.48 (m, 2H, CHCH$_3$), 1.26 (t, 3H, $OCH_2CH_3$), 1.20 (d, 3H, CHCH$_3$).

Ethyl threo-3-hydroxy-2-methyl-8-phenylnonanoate

NMR: δ 7.1–7.4 (m, 5H, ArH), 4.17 (q, 2H, $OCH_2CH_3$), 3.62 brs, 1H, CHOH), 2.60 (t, 2H, $CH_2$Ph), 2.50 (m, 2H, CHCH$_3$), 1.27 (t, 3H, $OCH_2CH_3$), 1.21 (d, 3H, CHCH$_3$).

Ethyl threo-3-hydroxy-2,5,9,13-tetramethyltetradecanoate

NMR: δ 4.17 (q, 2H, $OCH_2CH_3$), 3.75 (brs, 1H, CHOH), 2.54 (d, 1H, OH), 2.49 (m, 1H, CHCH$_3$).

2. E-3-Methyl-4-(6-phenylhexyl)-2-oxetanone

A mixture of ethyl threo-3-hydroxy-2-methyl-8-phenylnonanoate (110 mg) and 1 ml of 1.7M KOH in ethanol-$H_2O$ (1:1) was stirred at room temperature in a $N_2$ atmosphere for 3 hours. The clear solution was diluted with $H_2O$, extracted with $Et_2O$, acidified with concentrated HCl, and extracted with $Et_2O$ (3×). The combined $Et_2O$ extracts were washed with $H_2O$ and saturated brine and dried ($MgSO_4$). Evaporation in vacuo gave threo-3-hydroxy-2-methyl-8-phenylnonanoic acid.

A solution of threo-3-hydroxy-2-methyl-8-phenylnonanoic acid (88 mg, 0.33 mmole) in pyridine (2 ml) was cooled to $-15°$ C. and p-toluenesulfonyl chloride (127 mg, 0.66 mmole) was added. After stirring several minutes, the solution was kept at 3° C. for 20 hours. The red-brown solution was poured onto ice-cold $1M_2SO_4$-$Et_2O$. The aqueous phase was extracted with $Et_2O$ (2x). The combined $Et_2O$ phases were washed with $H_2O$ saturated $NaHCO_3$ solution, saturated brine, and dried ($MgSO_4$). The residue after evaporation in vacuo was purified by TLC (silica gel, hexane-EtOAc 9:1) to give E-3-methyl-4-(6-phenylhexyl)-2-oxtanone. IR 1822 cm$^{-1}$ (C=O); NMR: δ 7.1–7.4 (m, 5H, ArH), 4.16 (dxt, 1H, 4-H), 3.22 (dxq, 1H, 3-H, J 3,4=4.0 Hz), 2.60 (t, 2H, $CH_2$Ph), 1.38 (d, 3H, CHCH$_3$).

The following compounds were prepared using essentially the same method:

| Compound No. | |
|---|---|
| 2 | E-3-Methyl-4-decyl-2-oxetanone |
| | NMR: δ 4.18 (d×t, 1H, 4-H), 3.23 (d×g, 1H, 3-H, J 3,4,=4.0Hz), 1.41 (d, 3H, CHCH$_3$), 0.88 (t, 3H, CH$_3$CH$_2$). |
| 3 | E-3-Methyl-4-(5-phenylpentyl)-2-oxetanone |
| | IR 1825 cm$^{-1}$ (C=O); NMR: δ 7.1–7.35 (m, 5H, ArH), 4.15 (d×t, 1H, 4-H), 3.20 (d×g, 1H, 3-H, J 3,4=4.0 Hz), 2.61 (t, 2H, $CH_2$Ph), 1.37 (d, 3H, CHCH$_3$). |
| 4 | E-3-Methyl-4-(9-decenyl)-2-oxetanone |
| | NMR: δ 5.81 (m, 1H, CH=$CH_2$), 4.9–5.1 (m, 2H, CH=$CH_2$), 4.16 (d×t, 1H, 4-H), 3.20 (d×q, 1H, 3-H, J 3,4=3.9 Hz), 2.03 (q, 2H, CH2CH=), 1.37 (d, 3H, CH$_3$CH). |
| 5 | E-3-Methyl-4-(9-decynyl)-2-oxetanone |
| | IR 1825 cm$^{-1}$ (C=O), 2110 cm$^{-1}$(C=C). NMR: δ 4.17 (d×t, 1H, 4-H), 3.22 (d×q, 1H, J 3,4=4.0 Hz, 3-H), 2.19 (m, 2H, $CH_2$C=C), 1.94 (t, 1H, C≡CH), 1.38 (d, 3H, CHCH$_3$). |
| 6 | E-3-Methyl-4-(9-oxodecyl)-2-oxetanone |
| | NMR: δ 4.18 (d×t, 1H, 4-H), 3.21 (d×q, 1H J 3,4=4.0, 3-H), 2.42 (t, 2H, $\overset{O}{\underset{}{C}}$H$_2$C), 2.12 (S, 3H, CH$_3$$\overset{O}{\underset{}{C}}$), 1.38 (d, 3H, CH$_3$CH). |

EXAMPLE 7

Preparation of E-3-Methyl-4-(9-oxodecyl)-2-oxetanone

1. Threo-3-hydroxy-2-methyl-12-tridecynoic acid

To a solution of threo-3-hydroxy-2-methyl-12tridecenoic acid (420 mg, 1.74 mmoles) in $CH_2Cl_2$ (2 ml) cooled to 0° C. was added dropwise $Br_2$ (94 ml, 1.81 mmoles). The mixture was kept at room temperature for 10 minutes, and the solvent removed in vacuo to give the 12,13 dibromo compound.

A solution of the above dibromo compound in 3 ml of $Et_2O$ was added to a suspension of $NaNH_2$ (prepared from 220 mg of Na) in 15 ml of liquid $NH_3$. After stirring for 4 hours in a $N_2$ atmosphere, the $NH_3$ was allowed to evaporate overnight. The residue was dissolved in concentrated $NH_4OH$ (20ml) and filtered. The filtrate was washed with $Et_2O$, acidified with concentrated HCl and extracted with $Et_2O$ (3×). The combined Et₂O extracts were washed with H₂O and saturated brine and dried (MgSO₄). Evaporation in vacuo gave threo-3-hydroxy-2-methyl-12-tridecynoic acid.

NMR: δ3.70 (brs, 1H, C̲HOH), 2.56 (m, 1H, C̲HCH₃), 1.94 (t, 1H, C≡-CH), 1.24 (d, 3H, CHC̲H₃).

2. Threo-3-hydroxy-2-methyl-12-oxotridecanoic acid

A solution of threo-3-hydroxy-2-methyl-12-tridecynoic acid (160 mg, 0.67 mmoles) in 1 ml of 90% EtOH was stirred with 50 mg of Hg/Nafion-H [Synthesis, 671 (1978)] at room temperature for 8 hours and then at 43° C. for 30 minutes. The resin was filtered and washed EtOH (2x) and Et₂O (3x). The filtrate and washes were diluted with H₂O and extracted with Et₂O (3×). The combined Et₂O extracts were washed with H₂O and saturated brine and dried (MgSO₄). Evaporation in vacuo gave threo-3-hydroxy-2-methyl-12-oxotridecanoic acid.

NMR: δ 3.48 (brs, 1H, C̲HOH), 2.57 (m, 1H, C̲HCH₃), 2.42 (t, 2H, CH₂CO), 2.12 (s, 3H, COCH₃), 1.25 (d, 3H, CHC̲H₃).

3. E-3-Methyl-4-(9-oxodecyl)-2-oxetanone

Utilizing the general procedure of Example 1, Step 2, the above noted compound was obtained from threo-3-hydroxy-2-methyl-12-oxo-tridecanoic acid.

NMR: δ 4.18 (dxt, 1H, 4-H), 3.21 (dxq. 1H, J=4.0 H₂=Hz), 2.42 (t, 2H, CH₂CO), 2.12 (5, 3H, CH₃CO), 1.38 (d, 3H, CH₃CH).

EXAMPLE 8

Preparation of 8-(3-methoxymethyl-4-oxo-2-oxetanyl)-4-methyl-2-octanone

To a solution of 400 mg (1.135 mmole) of methyl 11-(3-methoxymethyl-4-oxo-2-oxetanyl)3,5,7-trimethyl-2,4-undecadienoate in 10 ml of CHCl₂ at −78° C., was bubbled ozone for 8 minutes. The resulting mixture was stirred for 30 minutes at −78° C. then at room temperature for another 30 minutes. Acetic acid and zinc dust were added. After stirring for 1 hour at room temperature, the solution was filtered and the filtrate was concentrated to dryness. The product was purified by flash column chromatography to give 8-(3-methoxymethyl-4-oxo-2-oxetanyl)-4-methyl-2-octanone as a colorless oil.

NMR: (CDCl₃) = δ 0.88 (d, 3H, 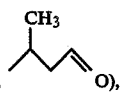 O), 2.12 (S, 3H, 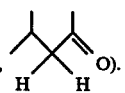 O), 2.22, 2.34 (d+d, 2H, O).

EXAMPLE 9

Preparation of 8-(3-methoxymethyl-4-oxo-2-oxetanyl)4-methyl-2-octanol 40 mg (0.156 mmole) of 8-(3-methoxymethyl-4-oxo-2-oxetanyl)-4-methyl-2-octanone in 5 ml of MeOH, was added 10 mg of sodium borohydride. The mixture was stirred for 5 minutes at room temperature. The product as purified by flash column chromatography (30%

ETOAc in hexane) to afford 8-(3-methoxymethyl-4-oxo-2-oxetanyl-4-methyl-2-oxetanol as an oil.

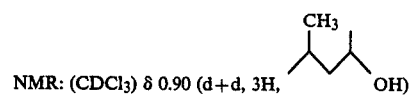

NMR: (CDCl₃) δ 0.90 (d+d, 3H, OH)

1.19 (d+d, 3H, OH), 1.80 (m, 2H, OH), 3.88 (q, 1H, OH).

EXAMPLE 10

Preparation of 8-(3-methoxymethyl-4-oxo-2-oxetanyl)-4-methyl-2-methoxyoctane 10 mg of 8-(3-methoxymethyl-4-oxo-2-oxetanyl)-4-methyl-2-octanol in 1 ml of EtOAc was added a small amount of activated silver oxide and 0.5 ml of methyl iodide. The mixture was heated for 5.5 hours at N 60° C. The solution was filtered and the filtrate was concentrated to dryness. The product was purified by flash chromatography to yield 8-(3-methoxymethyl-4-oxo-2-oxetanyl)-4-methyl-2-methoxyoctane.

NMR: (CDCl₃) = δ 0.87 (d+d, 3H, OCH₃), 1.11 (d+d, 3H, OCH₃), 3.32 (S, 3H, OC̲H₃),

EXAMPLE 11

Preparation of 11-(3-hydroxymethyl-4-oxo-2-oxetanyl)-4,5-oxiranyl-4,5,7-trimethyl-2-undecenoic acid 65 mg (0.20 mmole) of 11-(3-hydroxymethyl-4-oxo-2-oxetanyl)-3,5,7-trimethyl-2,4-undecadienoic acid in 3 ml of CH₂Cl₂ was added 0.12 mg (0.7 mmole) of m-chloroperoxybenzoic acid. The resulting mixture was strred for 2 hours at room temperature. The product was purified by prep. TLC (5% MeOH in CH₂Cl₂) to yield 11-(3-hydroxymethyl-4-oxo-2-oxetanyl)-4,5-oxiranyl-3,5,7-trimethyl-2-undecenoic acid.

NMR: (CDCl₃) = δ 1.14 (S, 3H, 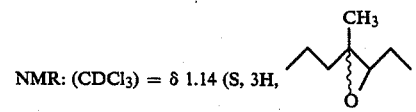

EXAMPLE 12

Preparation of Methyl-11-(3-hydroxymethyl-4-oxo-2-oxetanyl)-4,5-oxiranyl-3,5,7-trimethyl-2-undecenoate Similarly, following the procedure of Example 11, but substituting methyl 11-(3-hydroxymethyl-4-oxo-2-oxetanyl)-3,5,7-trimethyl-2,4-undecadienoate for 11-(3-hydroxoymethyl-4-oxo-2-oxetanyl)-3,5,7-trimethyl 2,4-undecadienoic acid yielded methyl 11-(3-(hydroxymethyl)-4-oxo-2-oxetanyl)-4,5-oxiranyl-3,5,7-trimethyl-2-undecenoate.

NMR: (CDCl$_3$) δ 1.14 (S, 3H, 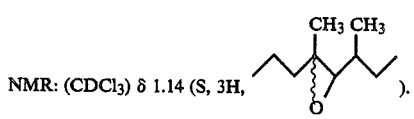 ).

Mass spectrum M/1=355 (m7).

EXAMPLE 13

Preparation of Methyl-11-(3-hydroxymethyl-4-oxo-2-oxetanyl)-4,5-dihydroxy-3,5,7-trimethyl-2-undecenoate To a solution of 20 mg (0.059 mmole) of methyl 11-(3-hydroxymethyl-4-oxo-2-oxetanyl)-3,5,7-trimethyl-2,4-undecadienoate in 3 ml of EtOAc at 0° C. was added 100 ml of pyridine, then added 200 ml of osmium tetroxide-ether solution (1 g/10 ml, 20 mg). The mixture was stirred for 1 hour at 0° C., then 1 hour at room temperature until the solution turned brown. The solution was concentrated to dryness. The residue was redissolved in 10 ml of CH$_2$Cl$_2$. The CH$_2$Cl$_2$ solution then was added to an aqueous sodium bisulfate solution (1 g in 8 ml of H$_2$O). The mixture was stirred overnight. The organic layer was separated, dried and concentrated. The product was purified by prep. TLC (hexane:EtOAc=1:1) to give methyl 11-(3-hydroxymethyl-4-oxo-2-oxetanyl)-4,5-dihydroxy-3,5,7-trimethyl-2-undecenoate.

NMR: (CDCl$_3$) = δ 1.14 (S, 3H, 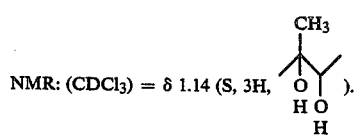 ).

EXAMPLE 14

Preparation of Methyl-11-(3-methoxymethyl-4-oxo-2-oxetanyl)-4,5-dihydroxy-3,5,7-trimethyl-2-undecenoate 10 mg of methyl 11-(3-hydroxymethyl-4-oxo-2-oxetanyl)-4,5-dihydroxy-3,5,7-trimethyl-2-undecenoate in 2 ml of EtOAc was added 35 mg of silver oxide and 0.3 ml of methyl iodide. The mixture was heated at 53° C. overnight. The solution was filtered and concentrated by dryness. The product was purified by prep. TLC (EtOAc:Hexane=1:1) to afford methyl 11-(3-methoxymethyl-4-oxo-2-oxetanyl)-4,5-dihydroxy-3,5,7-trimethyl-2-undecenoate.

NMR: (CDCl$_3$) δ 1.13 (S, 3H, 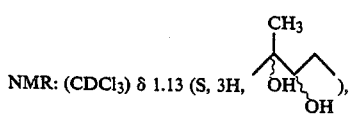 ), 3.40 (S, 3H, CH$_3$O  ).

EXAMPLE 15

Preparation of methyl-11-(3-methoxymethyl-4-oxo-2-oxetanyl)-3,5,7-trimethyl-2-undecenoate

1. Methyl 11-(3-hydroxymethyl-4-oxo-2-oxetanyl)-3,5,7-trimethyl-2-undecenaote 49 mg (0.144 mmole) of Methyl 11-(3-hydroxymethyl-4-oxo-2-oxetanyl)-3,5,7-trimethyl-2,4-undecadienoate in 5 ml of EtOAc was added 3 mg of platinium oxide. This mixture was hydrogenated at room temperature and 1 atom for N30 minutes (NO. 144 mmole (1 eq) of hydrogen was consumed). The solution was filtered and the filtrate was concentrated to dryness afforded methyl 11-(3-hydroxymethyl-4-oxo-2-oxetanyl)-3,5,7-trimethyl-2-undecenoate.

NMR (CDCl$_3$): δ 0.83(m,6H), 5.62(s,1H).

2. Methyl 11-(3-methoxymethyl-4-oxo-2-oxetanyl)-3,5,7-trimethyl-2-undecenoate Similarly, following the procedure of Example 16, Step 1, but substituting methyl 11-(3-methoxymethyl-4-oxo-2-oxetanyl)-3,5,7-trimethyl-2,4-undecadienoate for methyl 11-(3-hydroxymethyl-4-oxo-2-oxetanyl)-3,5,7-trimethyl-1,4-undecadienoate, afforded methyl 11-(3-methoxymethyl-4-oxo-2-oxetanyl)-3,5,7-trimethyl-2-undecenoate.

EXAMPLE 16

Preparation of Alkali and Alkaline Earth Salts of Compound I wherein R$^1$ is carboxy To a solution of the lactone from Example 1 (42 mg) in ethanol (2 ml) is added aqueous NaOH (1 equivalent). After one hour at room temperature, the mixture is taken to dryness in vacuo to yield the sodium salt of Compound I, wherein R$^1$ is carboxy.

In like manner, the potassium salt is prepared using one equivalent of potassium hydroxide, and the calcium salt using one equivalent of CaO.

EXAMPLE 17

As a specific embodiment of an oral composition of a compound of this invention, 20 mg of the lactone from Example 1 is formulated with sufficient finely divided lactose to provide a total amount of 580 to 590 mg to fill a size 0 hard gelatin capsule.

EXAMPLE 18

As a specific embodiment of a parenteral composition of a compound of this invention, 20 mg of the lactone from Example 1, as the sodium salt, is dissolved in sterile water, buffered to a pH of 7 with 1.0 mM potassium phosphate buffer solution to a concentration of 2.0 percent and is placed in a sterile ampule for parenteral administration.

What is claimed is:

1. A compound represented by the following structural formula (I):

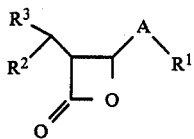 (I)

wherein:
R[1] is selected from
(1) hydrogen,
(2) hydroxy,
(3) $C_{1-6}$ alkoxy
(4) phenyl,
(5) carboxy,
(6) $C_{1-6}$ alkoxycarbonyl,
(7) substituted $C_{1-6}$ alkoxycarbonyl in which the substituent is a phenyl group,
(8) aminocarbonyl,
(9) $C_{1-6}$ alkylaminocarbonyl,
(10) substituted $C_{1-6}$ alkylaminocarbonyl in which the substituent is a hydroxy group,
(11) phenylaminocarbonyl,
R[2] is selected from
(1) hydrogen,
(2) $C_{1-6}$ alkyl,
(3) $C_{1-6}$ alkyloxy,
(4) $C_{2-6}$ alkenyloxy,
(5) formyloxy,
(6) $C_{1-6}$ alkylcarbonyloxy,
(7) carboxy $C_{1-6}$ alkylcarbonyloxy,
(8) anisyldiphenylmethyloxy,
(9) $C_{1-6}$ alkylsulfonyloxy,
(10) aminocarbonyloxy, and
(11) $C_{1-6}$ alkylaminocarbonyloxy;
R[3] is selected from
(1) hydrogen,
(2) $C_{1-6}$ alkyl,
(3) $C_{2-6}$ alkenyl,
(4) phenyl, or
R[2] and R[3] when taken together with the carbon atom to which the are attached form $C_{3-6}$ carbocyclic ring;
A is selected from
(1) $C_{6-17}$ alkylene,
(2) substituted $C_{6-17}$ alkylene in which the one or wwo substituents are
  (a) oxo,
  (b) epoxy,
  (c) geminal dihydroxy,
  (d) $C_{1-6}$ alkoxy, and
  (e) 4-bromophenylhydrazono;
(3) monounsaturated $C_{6-17}$ alkylene, and
(4) substituted monounsaturated $C_{6-17}$ alkylene in which the one or two substituents are
  (a) oxo,
  (b) epoxy,
  (c) geminal dihydroxy,
  (d) $C_{1-6}$ alkoxy, and
  (e) 4-bromophenylhydrazono;
(5) $C_{7-16}$ aralkylene, wherein the alkyl chain is interupted by a 1,2-, 1,3-, or 1,4-phenylene moiety, (6) $C_{6-18}$ alkylene, straight or branched chain, interupted by an oxygen, sulfur or sulfoxide moiety,
(7) a group of the structure

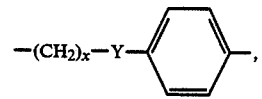

where x is 1–4 and Y is O, S, or SO; or a pharmaceutically acceptable salt thereof.

2. A compound of claim 1 wherein A is $C_{6-17}$ alkylene.

3. A compound of claim 2 which is E-3-methyl-4-(5-phenylpentyl)-2-oxetanone.

4. A compound of claim 2 which is E-3-methyl-4-(6-phenylhexyl)-2-oxetanone.

5. A compound of claim 2 which is E-3-methyl-4-(9-phenylnonyl)-2-oxetanone.

6. A compound of claim 2 which is E-3-methyl-4-decyl-2-oxetanone.

7. A compound of claim 1 wherein A is substituted $C_{6-17}$ alkylene.

8. A compound of claim 7 which is 8 -(3-hydroxymethyl-4-oxo-2-oxetanyl-4-methyl-2-octanone.

9. A compound of claim 7 which is 8-(3-hydroxymethyl-4-oxo-2-oxetanyl)-4-methyl-2-(4-bromophenylhydrazono)-octane.

10. A compound of claim 7 which is 8-(3-methoxymethyl-4-oxo-2-oxetanyl)-4-methyl-2-octanone.

11. A compound of claim 7 which is 8 -(3-methoxymethyl-4-oxo-2-oxetanyl)-4-methyl-2-methoxyoctane.

12. A compound of claim 7 which is 8-(3-methoxymethyl-4-oxo-2-oxetanyl)-4-methyl-2-octanol.

13. A compound of claim 7 which is E-3-methyl-4-(9-oxodecyl)-2-oxetanone.

14. A compound of claim 1 wherein A is monounsaturated $C_{6-17}$ alkylene.

15. A compound of claim 14 which is E-3-methyl-4-(9-decenyl)-2-oxetanone.

16. A compound of claim 1 wherein A is substituted monounsaturated $C_{6-17}$ alkylene.

17. A compound of claim 16 which is methyl 11-(3-hydroxymethyl-4-oxo-2-oxetanyl)-4,5-oxiranyl-3,5,7-trimethyl-2-undecenoate.

18. A compound of claim 16 which is 11-(3-hydroxymethyl-4-oxo-2-oxetanyl)-4,5-oxiranyl-3,5,7-trimethyl-2-undecenoic acid.

19. A compound of claim 16 which is methyl 11-(3-hydroxymethyl-4-oxo-2-oxetanyl)-4,5-dihydroxy-3,5,7-trimethyl-2-undecenoate.

20. A compound of claim 16 which is methyl 11-(3-methoxymethyl-4-oxo-2-oxetanyl)-4,5-dihydroxy-3,5,7-trimethyl-2-undecenoate.

21. A pharmaceutical composition for the treatment of hypercholesterolemia which comprises a non-toxic effective amount of a compound of claim 1 and a pharmaceutically acceptable carrier.

22. A method of inhibiting cholesterol biosynthesis which comprises the administration to a subject in need of such treatment a non-toxic therapeutically effective amount of a compound of claim 1.

* * * * *